United States Patent [19]

Compere et al.

[11] 4,287,305
[45] Sep. 1, 1981

[54] MICROORGANISM IMMOBILIZATION

[75] Inventors: Alicia L. Compere, Knoxville; William L. Griffith, Oak Ridge, both of Tenn.

[73] Assignee: The United States of America as represented by the United States Department of Energy, Washington, D.C.

[21] Appl. No.: 701,479

[22] Filed: Jun. 30, 1976

[51] Int. Cl.³ .................... C13N 11/14; C12N 11/08
[52] U.S. Cl. .................................. 435/176; 435/177; 435/180
[58] Field of Search ................. 195/63, 68, DIG. 11, 195/57, 59, 54, 116; 435/174, 176, 177, 180, 181

[56] References Cited

U.S. PATENT DOCUMENTS

| 3,242,073 | 3/1966 | Guebert | 210/64 |
|---|---|---|---|
| 3,796,634 | 3/1974 | Haynes et al. | 195/63 |
| 3,849,253 | 11/1974 | Harvey et al. | 195/68 |
| 3,860,490 | 1/1975 | Guttag | 195/57 |
| 3,915,797 | 10/1975 | Ishimatsu et al. | 195/116 X |
| 3,957,580 | 5/1976 | Nelson | 195/59 |
| 3,972,776 | 8/1976 | Vieth et al. | 195/63 X |
| 4,009,286 | 2/1977 | Moll et al. | 195/116 X |
| 4,032,407 | 6/1977 | Scott et al. | 195/116 X |

OTHER PUBLICATIONS

Atkinson et al., The Completely Mixed Microbial Film Fermenter, Trans. Instn. Chem. Engrs., vol. 50, 1972 (pp. 208–216).

Primary Examiner—David M. Naff
Attorney, Agent, or Firm—John B. Hardaway; David S. Zachry; James E. Denny

[57] ABSTRACT

Live metabolically active microorganisms are immobilized on a solid support by contacting particles of aggregate material with a water dispersible polyelectrolyte such as gelatin, crosslinking the polyelectrolyte by reacting it with a crosslinking agent such as glutaraldehyde to provide a crosslinked coating on the particles of aggregate material, contacting the coated particles with live microorganisms and incubating the microorganisms in contact with the crosslinked coating to provide a coating of metabolically active microorganisms. The immobilized microorganisms have continued growth and reproduction functions.

4 Claims, No Drawings

MICROORGANISM IMMOBILIZATION

BACKGROUND OF THE INVENTION

This invention was made in the course of, or under, a contract with the Energy Research and Development Administration. It relates generally to the art of immobilizing microorganisms.

Microorganisms vary greatly in their ability to attach themselves to solid material. Some microorganisms attach well to solids of biological origin. Some microorganisms even attach readily to artificial materials. Certain microorganisms form their own slimes upon solids to serve the purpose of producing growth sites. Most organisms, however, particularly the anaerobic microorganisms, have a rate of attachment to solids that is extremely slow and in some cases almost imperceptible.

In many systems it is highly desirable to have whole microorganisms attached to a support as opposed to the enzymes which the microorganisms produce. By so doing costly enzyme purification is avoided. Prior art techniques for achieving this result have immobilized microorganisms in an inactive or dead form. This technique is highly useful in many fields of endeavor. This method of attachment, however, tends to produce a support which has a lower enzyme activity than the live microorganisms. The use of inactive or dead microorganisms does not confront the problem of slow growth rate and attachment of live microorganisms.

SUMMARY OF THE INVENTION

It is thus an object of this invention to provide a process for immobilizing whole cell microorganisms.

It is a further object of the invention to provide a process for immobilizing whole cell microorganisms wherein the whole cells are alive and remain metabolically active with continued growth and reproduction functions.

It is a still further object of this invention to provide an article to which microorganisms will readily attach.

It is a still further object of this invention to provide such an article which promotes and encourages the rapid growth or culturing of the microorganism of interest when in the presence of appropriate nutrients.

These as well as other objects are accomplished by coating an aggregate support with a polyelectrolyte and crosslinking the polyelectrolyte to create a coating environment conducive to bacterial growth and life.

DETAILED DESCRIPTION

According to this invention it has been found that aggregate material may be treated by the process of this invention to produce a coating which is compatible with and conducive to anaerobic microorganism growth and existence. The technique for producing a growth stimulating and metabolically compatible coating comprises contacting conventional aggregate material with a polyelectrolyte and then crosslinking the polyelectrolyte by reacting it with a crosslinking agent.

Various shapes of aggregate material may be used in the process of this invention. These materials include conventional materials used for distillation and catalyst support reactions, such as pellets, stars, spiral rings, cross partition rings, raschig rings, berl and intalox saddles, pall rings, tellerette rings (flexirings), spheres, and irregular spheroids. The aggregate material can be composed of any conventional support material such as metals, ceramics, including both porcelain and stoneware; clay ceramics, including pottery clays; plastics, including polyethylene, polypropylene, and nylon; glass; woods, such as redwood; stones; cement and cement aggregates.

Live microorganisms can be attached to the crosslinked coating either during the crosslinking reaction or after. If attached during the crosslinking reaction, the microorganisms are locked within the crosslinked network. However, even with this locking in of the microorganism, the metabolic and growth activities of the microorganisms are not impaired. To the contrary, the growth and metabolic activity have been found to be surprisingly enhanced by the crosslinked coating environment. This advantage, however, is not limited to the coatings which have organisms attached during the crosslinking process but is present to the same extent in coatings which are crosslinked prior to contacting with the live microorganisms. Preferably, the crosslinked polyelectrolyte coating is selected so that it will have, across the pH range planned for use, a charge opposite to that found on the microorganisms across the same pH range. Where this is not possible, a second polyelectrolyte may be used either with the first polyelectrolyte or on the surface of the microorganisms, to provide a charge which is compatible with both the first polyelectrolyte and the microorganism.

The materials used in forming the coating of this invention are thus divided into a polyelectrolyte and a crosslinking agent. These materials form a coating on virtually any relatively inert material. The polyelectrolyte may be selected from the group consisting of gelatin, egg albumin, hide pulp collagen, refined collagen, fibrin, gluten and acrylic acid derivatives such as polyacrylamide and poly(hydroxy-ethyl methacrylate) and copolymers thereof. The polyelectrolyte may thus be crosslinked with a crosslinking agent to be insolubilized and to form a crosslinked coating. The crosslinking agent may be selected from the group consisting of glutaraldehyde, ethylchloroformate, formaldehyde, dimethyl adipimidate, N,N'-methylenebisacrylamide, 1,2-diacrylamide ethyleneglycol, N,N'-diallyltartardiamide, cyanogen bromide, concanavalin A, 6-aminohexanoic acid, 1-6-diaminohexane, and compounds having similar functional crosslinking groups but different chain lengths. The method of coating formation includes the preparation of a suspension or solution of the polyelectrolyte, together with such additional chemicals as may be deemed beneficial or necessary. The chemicals which are added to a polyelectrolyte suspension include chemicals, such as a secondary polyelectrolyte, which is added in order to give the solution or suspension desirable physical properties, such as a higher or lower viscosity; chemicals which are added in order to give the solution desirable chemical properties, such as a second polyelectrolyte which is added for the purpose of modifying the charge of the first polyelectrolyte in such a fashion as to produce a solution having an appropriate average charge; compounds which decrease the toxicity of the solution to the organisms being encapsulated, such as glycerol; small molecules, such as ferric chloride, which promote the mechanical strength of the crosslinked polyelectrolyte by providing cation or anion bridges between adjacent polymer strands; and the addition of chemicals, such as pennicillin and streptomycin, which inhibit the growth of undesired organisms in or on the hydrogel; i.e. the crosslinked coating.

The degree of crosslinking of the resulting coating is not critical. The higher the percentage of crosslinking the harder, of course, will be the coating. The degree of crosslinking can be somewhat ascertained by taking into consideration the fact that the site size should correspond to the size of the microorganisms which are generally within the range of 0.25 to 40 micrometers. As above stated the degree of crosslinking is not critical but a mixture comprising 10 volume percent polyelectrolyte and about 0.1 to 10 volume percent crosslinking agent is satisfactory for producing an article in accordance with this invention. Generally, it is preferred to have sufficient crosslinking agent to provide one carboxylic linking group from the crosslinking agent for every available amine group of the polyelectrolyte. About a 10 percent excess of crosslinking agent provides sufficient carboxylic acid linking groups to fulfill this condition.

The solution or suspension is then applied to the surface of the material to be coated using conventional methods, such as spraying, dipping, rolling, or painting. After application of the polyelectrolyte crosslinking is commenced. Under some conditions, crosslinking can be performed immediately prior to the application of the polyelectrolyte solution to the objects to be coated. In some cases, a stabilized form of polyelectrolyte, produced by, for example, microencapsulation, can be combined with a crosslinking agent, and an agent which releases the polyelectrolyte can be employed either at the time of application or immediately thereafter. Some polyelectrolytes, such as "Nalco" 8172, are supplied in a microencapsulated form to provide a decreased viscosity of the solution supplied.

A second polyelectrolyte, together with the microorganisms can be added and the crosslinking process repeated. If desired, both polyelectrolytes and the microorganisms can be added and crosslinked concurrently. Charged microorganisms coated with the second polyelectrolyte can be added to a solution circulating around the packing coated with the first polyelectrolyte after the first polyelectrolyte has been crosslinked. By virtue of charge, the second polyelectrolyte and the microorganisms will adhere to the crosslinked coating on the surface.

There are a variety of methods whereby microorganisms can be contacted for attachment to the packing material. One method comprises passing the microorganism suspension, in a liquid phase, through a bed of packing to which the crosslinked polyelectrolyte has been attached. This may be done by passing the liquid phase either up or down through the packed bed. Another method involves the deposition of the microorganism on the packed bed either through spraying or through other means of depositing small amounts of material evenly on the surface of the hydrogel. This may be done with the microorganisms either in a liquid suspension or a dry, finely divided form. During this process, the packing material and the hydrogel can be either wet or dry. The dry forms may be desirable where the coated packing material with the included microorganisms will be shipped or stored for a substantial period of time.

The major elements in the contacting of the microorganisms with the coating are the even coating of finely divided microorganisms either suspended in air or in a suitable liquid medium so that they arrive at the surface of the coating under conditions which promote the adherence of the microorganisms. Such conditions include provisions for appropriate physical considerations, such as temperature, and shear stress, for the adherence and growth of the microorganisms.

Having generally described the process and coating produced thereby embodied within the scope of this invention, the following specific examples are given as a further illustration thereof.

EXAMPLE I

Glass squares, 15 mm on a side, were spray coated with different materials and combinations of materials. The materials included a 10% w/v solution of gelatin (Preiser); a 1% w/v solution of Nalco 8172 polyelectrolyte; and a 5% w/v solution of champagne yeast, with and without 1% added ferric chloride. The materials were sprayed in a thin layer onto the glass plates, and crosslinked with a spray of 5% w/v glutaraldehyde. The plates were then dried for a period of 24 hours at room temperature. In some cases, the yeasts used were not sprayed onto the coating but were added to the incubation mixture at a rate of 1 ml of a 5% w/v yeast solution per liter. Randomly labeled glucose-$^{14}C$ was then added at a rate of 1 $\mu$Ci/liter of medium.

The yeast plates were incubated in a medium containing 5% glucose, 0.5% tryptone, and 0.1% $NaH_2PO_4$ w/v for periods of 1 and 4 days at 30 C. The plates were then removed from the medium and washed in 3 to 10 ml rinses of 5% w/v cold trichloroacetic acid. They were counted in a Packard Tricarb model 3375 scintillation counter in a scintillation fluid composed of 770 ml xylene, 770 ml p-dioxane, 460 ml absolute ethanol, 160 g napthalene, 10 g PPO (Packard), and 0.10 g POPOP (Packard). Yeast from the growth medium around the plates was centrifuged at 10,000 rpm for 10 min in a Sorvall SS-34 rotor. The supernatant medium was removed, and the yeast was suspended in 10 ml of cold 5% w/v trichloroacetic acid and filtered through a Whatman GF/C 45-mm filter. The filter was washed with two rinses of 10 ml of cold 5% w/v trichloroacetic acid. The filter was then counted as described above.

EXAMPLE II

The fermentation of waste whey from the manufacture of cottage cheese to produce lactic acid was demonstrated using an anaerobic upflow packed bed bioreactor utilizing the coating of this invention. It was desirable to treat the whey, using some type of a continuous fermentation system, since there are a variety of problems involved in the storage and handling of large volumes of whey for extended periods of time.

A columnar bioreactor using gelatin-coated packing crosslinked with glutaraldehyde was prepared. The column unit was two inches in diameter by six feet high, and was packed with ¼ inch berl saddles. The composition of the packing coating was produced using the same technique used for the glass square coating. A solution having the following constituents was prepared:

10% gelatin w/v
1% Nalco 8172 polyelectrolyte w/v
.5% glutaraldehyde
balance water Fifty milliliters of the solution was stirred with about one quart of packing material, ¼ inch berl stoneware saddles, for a period of several hours until there was no glutaraldehyde odor. The packing was then dried. The packing was seeded with a mixed culture containing lactobacilli and lactose-fermenting yeasts derived from a commercial kefir culture. The unit was fed for several weeks on reconstituted dried sweet whey made to a concentration of 5% solids. It was then tested using a sour cottage cheese whey. The reactor was operated in an upflow mode at flow rates between four and eight liters per day. This value corresponds to a superficial retention period of 10 to 20 hours, although the actual retention period was lower due to the accumulation of biological solids in the reactor. Sample taps were provided every foot vertically so that changes in the whey column could be observed as it passed through the column. The product from the packed-bed reactor was passed through a bed containing 150 grams (dry weight) of Rohm and Haas IRA-94 macroporous weak anion exchange resin. The column containing the resin was a 2.5 cm by 100 cm column, allowing for nearly 100% bed expansion during washing. The fermented whey was passed through the resin bed until breakthrough occurred. When the excess whey was drained from the bed, and the resin bed was washed upflow with distilled water at a flow rate that gave nearly 100% bed expansion for a period of at least ten minutes. Then 200 ml of a 5% w/v solution of calcium oxide was passed through the resin, and the product recovered as calcium lactate. The column was then washed at 100% bed expansion with distilled water, rinsed briefly with a 1% NaCl solution, washed with distilled water, and placed on line again.

The product was crystallized by permitting the calcium lactate solution to evaporate at room temperature. The product recovered was a fine efflorescent white crystalline material.

Where it was desirable to recover the products from the ion exchange unit as acids, the unit was stripped with a strong acid, such as sulfuric acid, and the acid rinse together with a distilled water chaser, used for measurements of product recovery. Following strong-acid stripping, the resin can be regenerated in the manner described above.

Lactic acid was determined using a Varian 940 gas chromatograph having a flame ionization detector. The chromatograph was equipped with a ⅛ inch by 2 meter column filled with Porpak P and maintained at a temperature of 140 C. Nitrogen was used as a carrier gas, and hydrogen and breathing air were used to provide the flame.

Samples were prepared by mixing 1 ml of sample with 0.1 ml of $H_3PO_4$. Standards, using reagent-grade lactic acid, were prepared in a similar fashion. Five microliters of the acid/sample mixture were injected into the column for lactic acid measurement.

There was a 1.4% lactic acid concentration in the sour whey which was used. This amount was increased after a single passage through the packed column, and reached a maximum of 2.1% after passage through the six-foot column. Following passage through the unit, the whey was stripped of its lactic acid using IRA-94 resin, which was produced by Rohm and Haas. The resin was stripped with 1 N sulfuric acid, and the lactic acid concentration in the acid-wash/water rinse was determined using a gas chromatograph. The lactic acid effluent from the resin was at a concentration of 1.7%. The acid rinse and water rinse had a volume of 1 liter. The total yield was 17 grams of lactic acid from 1300 ml of whey, which is equivalent to 62% recovery of lactic acid by the resin.

What is claimed is:

1. A process for producing an aggregate support material coated with a crosslinked coating, said coating having live, metabolically active microorganisms attached thereto, comprising the steps of:
   contacting a particle of aggregate material with a water dispersible gelatin;
   crosslinking said gelatin by reacting it with a glutaraldehyde to provide a crosslinked coating on said particle of aggregate material;
   then contacting said coated particle with live microorganisms; and
   then incubating said microorganisms in contact with said crosslinked coating to provide a coating having metabolically active microorganisms attached thereto, said microorganisms having continued growth and reproductive functions.

2. The process according to claim 1 wherein said particle of aggregate material is composed of a material selected from the group consisting of metals, porcelain, stoneware, glass, polyethylene, polypropylene, nylon and styrene.

3. The method of claim 1 in which said microorganisms are anaerobic.

4. An aggregate support material coated with a glutaraldehyde crosslinked gelatin coating having live metabolically active microorganisms attached thereto, said microorganisms having continued growth and reproductive functions.

* * * * *